(12) United States Patent
Bazito et al.

(10) Patent No.: US 10,603,524 B2
(45) Date of Patent: Mar. 31, 2020

(54) COMPLEX FOR IMPROVEMENT OF DISTRIBUTION AND RETENTION OF FRAGRANCES INTO KERATINOUS MATTER, USES, COSMETIC PRODUCT AND METHOD FOR IMPROVEMENT OF DISTRIBUTION AND RETENTION OF FRAGRANCES INTO KERATINOUS MATTER

(75) Inventors: Alexandra Bazito, São Paulo (BR); Liliana Calore Brenner, São Paulo (BR); Maria Regina Bartuccio Raponi, São Paulo (BR)

(73) Assignee: ISP Investments LLC, Wilmington, DE (US)

( * ) Notice: Subject to any disclaimer, the term of this patent is extended or adjusted under 35 U.S.C. 154(b) by 181 days.

(21) Appl. No.: 14/128,262

(22) PCT Filed: Jul. 5, 2012

(86) PCT No.: PCT/BR2012/000234
§ 371 (c)(1),
(2), (4) Date: Apr. 4, 2014

(87) PCT Pub. No.: WO2013/003928
PCT Pub. Date: Jan. 10, 2013

(65) Prior Publication Data
US 2014/0219943 A1 Aug. 7, 2014

(30) Foreign Application Priority Data
Jul. 7, 2011 (BR) .................................... 1103640

(51) Int. Cl.
*A61Q 5/02* (2006.01)
*A61K 8/34* (2006.01)
*A61Q 13/00* (2006.01)
*A61K 8/49* (2006.01)
*A61Q 5/12* (2006.01)

(52) U.S. Cl.
CPC ............... *A61Q 5/02* (2013.01); *A61K 8/342* (2013.01); *A61K 8/345* (2013.01); *A61K 8/4913* (2013.01); *A61Q 5/12* (2013.01); *A61Q 13/00* (2013.01)

(58) Field of Classification Search
None
See application file for complete search history.

(56) References Cited

U.S. PATENT DOCUMENTS

| | | | |
|---|---|---|---|
| 4,775,527 A | 10/1988 | Bires | |
| 4,954,335 A | 9/1990 | Janchipraponvej | |
| 6,619,295 B1 | 9/2003 | Okabe et al. | |
| 2006/0045914 A1 | 3/2006 | Narayanan | |
| 2006/0079422 A1* | 4/2006 | Midha | A61K 8/0237 510/130 |
| 2007/0117729 A1* | 5/2007 | Taylor et al. | 510/130 |

FOREIGN PATENT DOCUMENTS

JP 2002/161020 A 6/2002

OTHER PUBLICATIONS

International Search Report, PCT/BR2012/000234 published on Jan. 10, 2013.
Extended European Search Report, PCT/BR2012/000234 published on Oct. 20, 2014.

* cited by examiner

*Primary Examiner* — Nannette Holloman
(74) *Attorney, Agent, or Firm* — William J. Davis; Nathalie Tietcheu

(57) ABSTRACT

The present invention refers to a complex for the improvement of distribution and retention of fragrances into keratinous matter comprising (a) C10-C18 alkyl pyrrolidone, (b) at least one polyol compound and (c) at least one fatty alcohol, as well as uses, products, and related methods. The complex of the present invention homogeneously distributes fragrance into the keratinous matter, achieving a better interaction between the fragrance and the keratinous substrate, and better and longer perception of it, ensuring greater durability of the fragrance.

16 Claims, 1 Drawing Sheet

COMPLEX FOR IMPROVEMENT OF DISTRIBUTION AND RETENTION OF FRAGRANCES INTO KERATINOUS MATTER, USES, COSMETIC PRODUCT AND METHOD FOR IMPROVEMENT OF DISTRIBUTION AND RETENTION OF FRAGRANCES INTO KERATINOUS MATTER

CROSS REFERENCE TO RELATED APPLICATIONS

This application is the national stage of PCT Application No. PCT/BR2012/000234 filed Jul. 5, 2012, which claims priority from Brazilian Patent Application No. PI 1103640-0, filed Jul. 7, 2011, the entire disclosures of which are hereby incorporated in their entirety.

FIELD OF THE INVENTION

The present invention is included in the cosmetic area and it refers to a complex to improve the distribution and retention of fragrances into keratinous matter comprising (a) a $C_{10}$-$C_{18}$ alkyl pyrrolidone, (b) at least one polyol compound and (c) optionally at least one fatty alcohol.

PRIOR ART

The technology related to perfumes is very multifaceted. The olfactory perception is caused by the presence of odor molecules in the air, which are formed from the evaporation of volatile liquids that are included in the product composition. Thus, the nature, concentration and behaviors of these substances are important factors to be considered during the fragrance development and its inclusion into the various cosmetic bases.

In general, the one skilled in the art knows and understands the fragrance liquid mixture, but this is not true in relation to components formed after the evaporation, i.e. the ones that are responsible for the good odor. The same is true regarding the behavior of these substances with each other, and in relation to other ingredients included in the various cosmetic bases.

Although physic-chemical concepts can be helpful and several improved technologies are already available to help forecast the performance of these raw materials (e.g., headspace analysis), rarely there is accuracy. For this reason, the behavior of fragrances has also been estimated from a historical database of the behavior of mixtures of different batches, product types, substrates, among others, which makes the search for note harmony almost handmade.

In addition, we have to consider that besides the right balance in terms of perfumery, factors such as substantivity, distribution and retention are also important. This is because the longevity of the fragrance is a highly required property.

Therefore there is a search for fragrances in balance or harmony, particularly between its vapor pressure, liquid phase, interaction with the substrate where it will be applied and its polarity.

In this sense, when dealing with deficiencies in terms of distribution and fixation, some alternatives have been proposed. Majority refers to the use of specific compounds (binding agents) or pre-complex mixtures.

Patent application US2005/0032655, published in 2005, for example, reveals a fragrance delivery system for use in non-keratinous substrates comprising a micro emulsion concentrate, which contains several ingredients, among them non-ionic surfactant, $C_8$-$C_{18}$ and $C_1$-$C_4$ alkyl pyrrolidones, block copolymer of ethylene oxide/propylene and ethoxylated phosphoric acid ester.

However, many raw materials, which allow increasing the contact area of the fragrance substances, have a higher affinity with washing water than keratin substrate, due to their polar characteristics. Examples include molecules with a high degree of ethoxylation, very common in micro emulsions, which draw the fragrance in the wash process, allowing lower attachment.

Other more non-polar components, which have lower affinity with water, allow a better affinity with the grease present in the substrate, however, complicate the volatilization of certain starting materials, hindering the fragrance opening and thus reducing the user perception of the odor on the substrate. In addition, more non-polar components are likely to cloudy the transparent cosmetic bases.

Thus, there remains the need for new raw materials for cosmetics that promote better interaction between fragrance and keratinous substrates, allowing better and prolonged olfactory perception.

DESCRIPTION OF THE INVENTION

Figure 1:
FIG. 1 shows the scale of intensity of perfume used in the study.

In order to improve the perception of the distribution and fixing of fragrances into keratinous substrates, such as hair, a complex composition was developed which increases the perception of the fragrance for initial and long time when it is applied to the substrates, even when the cosmetic product is for the rinse.

Thus, the present invention refers to a complex for the improvement of distribution and retention of fragrances into keratinous matter comprising (a) $C_{10}$-$C_{18}$ alkyl pyrrolidone, (b) at least one polyol compound and (c) optionally at least one fatty alcohol.

Surprisingly, from the use of a specific combination of components known in the art, it was found that the complex according to the present invention not only homogeneously distributes (delivering) fragrance substances, but also provides simultaneous improved immediate and long lasting perfume perception.

The complex according to the present invention provides an interaction between the fragrance and the keratinous substrate, so that a greater percentage of retention of the perfume on the substrate can be achieved in comparison with the direct and/or conventional dispersion system of the fragrance in the cosmetic base.

The complex according to the present invention is useful in cosmetic area, particularly for application to keratinous substrates. It is understood by keratinous substrates all element that are made of keratin, without limitation, particularly skin, nails, hair, eyebrows, eyelashes, mustache, beard for human or animal body or synthetic substrates.

The complex also has the fragrance wetting function, i.e., allows, as a mixture, it associates more efficiently to the substrate, since the complex has polarity closest to the substrate than the water, especially the hair fiber, allowing the fragrance prefers substrate instead of water in the cosmetic formulation and/or rinsing water after application. Thus, the complex according to the present invention is especially advantageous for use in rinse-off products.

According to the present invention the improvement of distribution and retention of the fragrance is possible due to the fact that the complex provides an interaction between the fragrance and $C_{10}$-$C_{18}$ alkyl pyrrolidone, particularly lauryl pyrrolidone, which also acts as an emulsifier, as well as with the other ingredients of the complex, also allowing that when the mixture "complex+fragrance" is incorporated in the cosmetic base, such as in a shampoo, micro emulsion particles are obtained, which guarantee an increase in contact area and thus providing greater interaction with the substrate composed of keratin.

The amount of $C_{10}$-$C_{18}$ alkyl pyrrolidone particularly ranges from about 10 to about 60% by weight in relation to the total amount of the complex. Particularly, the amount ranges from about 40 to about 60%, more particularly about 50% by weight.

In the present specification, when not otherwise indicated, the percentages by weight indicated for certain ingredient are related to the total weight of the final product.

The term polyol or polyalcohol in the context of the present invention contemplates compounds containing one or more hydroxyl groups, including glycol compounds having at least two hydroxyl groups, such as ethylene glycol, butylene glycol or propylene glycol or having at least three hydroxyl groups, such as 1,2,3-propanetriol. In a particular manner, the present invention contemplates a mixture of propylene glycol (two hydroxyl groups), 1,2,3-propanetriol (three hydroxyl groups) in a 1:1 ratio.

The amount of polyol employed in the complex according to the present invention ranges from about 10 to about 60% by weight relative to the total amount of the complex. In a particular manner, the amount ranges from about 40 to about 60%, more particularly about 50% by weight.

The fatty alcohol is particularly selected from those having carbon chain from $C_{10}$ to $C_{22}$, being preferred alcohols selected from behenic, cetearyl or isocetyl, particularly in combination in amounts ranging from 10 to 30% by weight. It is especially advantageous to use a raw material consisting of a mixture of behenic alcohol, cetearyl alcohol and hydroxyethyl cetearamidopropyl dimonium chloride, sold under trademark Propilid 161 by ISP Corporation (U.S.).

The mixture of complex and fragrance also provides changes in the boiling point of the fragrance components, what further provides the delay of such ingredients in the liquid phase, taking longer to be transferred to the vapor phase and thus ensuring the extension of the perception of a harmonized fragrance.

The manufacturing of the complex composition is also simple, i.e., dispensing sophisticated processes, simply by mixing the ingredients in the proportions according to the invention.

The complex according to the present invention is suitable for a wide variety of fragrances, either as an additive that provides improved distribution and retention of the fragrance for direct application to keratinous matter, or preparation of cosmetic products in general, with rinse or not.

Accordingly, other objects of the present invention are the use of the complex as an additive that provides the effects discussed above in the preparation of cosmetic products and cosmetic products containing thereof. These are prepared with cosmetically acceptable excipients to obtain a cosmetic product, such as shampoos, creams, ointments, pastes, emulsions, gels, soap bar or liquid, serums, conditioners, lotions, perfumes, fragrances, colognes, combined cosmetic forms or other forms known in the art.

It is also object of the present invention the method for improving the distribution and retention of fragrances in substrates consisting of dilution of at least one fragrance in the complex according to the present invention prior to application to the keratinous substrate or cosmetic product.

Particularly, the amount of complex relative to the amount of fragrance to be used ranges from 0.01% to 99.99%. More particularly, it is used ratios between 1:0.5 and 0.5:1, preferably ratios from 1:1 to 0.75:1.

EXAMPLES

The following examples illustrate aspects of the invention without any limiting character.

Example 1

Complex According to the Invention

The table below shows variations of the complex formulation in accordance with the present invention according described in the specification. Said complex was prepared by mixing the ingredients in the amounts indicated.

TABLE 1

| Formulation - Complex 1 | | |
| --- | --- | --- |
| Ingredient | Trade Name | wt % |
| Propylene glycol | propilenoglicol | 25 |
| 1,2,3-propanetriol | glicerina | 25 |
| C12-pyrrolidone | Surfadone LP 300 | 50 |

TABLE 2

| Formulation - complex 2 | | |
| --- | --- | --- |
| Ingredient | Trade Name | wt % |
| Propylene glycol | propilenoglicol | 45 |
| Isocetyl alcohol | Ceraphyl ICA | 5 |
| C12-pyrrolidone | Surfadone LP 300 | 50 |

TABLE 3

| Formulation - complex 3 | | |
| --- | --- | --- |
| Ingredient | Trade Name | wt % |
| Isocetyl alcohol | Ceraphyl ICA | 10 |
| 1,2,3-propanetriol | Glicerina | 55 |
| C12-pyrrolidone | Surfadone LP 300 | 20 |
| Behenic alcohol/cetearyl alcohol/hydroxyethyl cetearamidopropyl dimonium chloride | Prolipid 161 | 15 |

TABLE 4

| Formulation - complex 4 | | |
| --- | --- | --- |
| Ingredient | Trade Name | wt % |
| Isocetyl alcohol | Ceraphyl ICA | 5 |
| 1,2,3-propanetriol | glicerina | 22.5 |
| Propylene glycol | propilenoglicol | 22.5 |
| C12-pyrrolidone | Surfadone LP 300 | 50 |

Surfadone LP 300, Ceraphyl ICA and Prolipid 161 are raw materials commercialized by ISP Corporation (U.S.).

Features of complexes 1-4:

Physical Appearance: transparent liquid pH: 5.00 to 9.00

Example 2

Manufacturing of Cosmetic Products Containing Complexes 1-4 from Example 1

The following tables show different cosmetic products in the form of shampoo containing the complexes as shown in Example 1 above.

TABLE 5

Shampoo Formulations - Samples A to D

|  | Complex 4 | Complex 3 | Complex 2 | Control |
|---|---|---|---|---|
| Amount of complex according to the present invention | 1.00 | 1.00 | 1.00 | 0.00 |
| Shampoo Formulation | A | B | C | D |
| Sodium lauryl ether sulfate (SLES) - 28% | 30 | 30 | 30 | 30 |
| Preservative - Ophthiphen | 0.8 | 0.8 | 0.8 | 0.8 |
| Amide 90 | 3.0 | 3.0 | 3.0 | 3.0 |
| Coco ampho betaine - 50% | 3.0 | 3.0 | 3.0 | 3.0 |
| Fragrance FAV 091191 | 1.5 | 1.5 | 1.5 | 1.5 |
| Water | qs | qs | qs | qs |

Ophthiphen is a raw material commercialized by ISP Corporation (U.S.) and FAV 091191 is a fragrance commercialized by FAV 105 and manufactured by Firminich.

TABLE 6

Shampoo Formulation - Samples E to F (Complex 4)

| Shampoo Formulation | E | F |
|---|---|---|
| Cocoamido propyl betaine | 3.00 | 3.00 |
| Amide 90 | 3.00 | 3.00 |
| Sodium lauryl ether sulphate | 30.00 | 30.00 |
| Water | QS | QS |
| Fragrance FAV 091191 | 1.50 | 1.50 |
| Complex - Formulation 4 | 0.00 | 1.00 |
| Citric Acid | 0.10 | 0.10 |
| Sodium chloride | 0.25 | 0.15 |

Features:

| pH | 6.50 24° C. | pH 6.19 24° C. |
|---|---|---|
| viscosity | 5,010 cps spindle 64 6 rpm | 5,230 cps spindle 64 6 rpm |

FAV 091191 is a fragrance commercialized by FAV 105 and manufactured by Firminich.

Efficiency Tests

Example 3

Study of the Functional Properties of the Complex 1 in a Base Containing Lauryl Ether Sodium Sulfate (LESS)

Effect of Complex 1 in the Intensity and Longevity of the Substantivity of the Fragrance in Capillary Substrate Perfumery raw materials as well as combinations therefore to produce fragrances were applied in strands of Caucasian hair. The components were first diluted to 1% in 10% SLES solution, in two groups of samples, the first containing 1% of the complex 1 used as a pre-dispersing for fragrance and its raw materials and the second not (control group).

Then each sample was applied on a strand and rinsed. Immediately after rinsing, as well as after 24 hours and 48 hours, the strands were evaluated by six volunteers.

The procedure was used to evaluate the interference of the complex in the fragrance substantivity, as well as the longevity of its perception.

Experiment

Caucasian hair strands (International Hair Imports), divided into four groups of two strands, one used as control and the other as sample. A specific fragrance raw material group was applied in the in the three groups of strands.

It was applied 1% citrol in 10% SLES in the first group, 1% limonene in 10% LESS in the second group, 1% linalool in 10% LESS in the third group, and 1% fragrance in the fourth group (containing the three previous cited ingredients). It was applied a solution without complex in the strand used as control and the component pre-dispersed in the complex 1 (1:1) in 10% SLES solution was applied in another one.

Then the treated strands were evaluated for comparative olfactory by a group of six volunteers, after washing, 24 hours after washing and 48 hours after washing.

Experiment Design

Objective: to compare standard Caucasian strands—International Hair Importers & Products Inc. (IHIP). IHIP treated with 10% LESS formulation used as reference without complex 1 with washing versus IHIP treated with 10% LESS formulation in the same percentage of the fragrance component with washing, initially, after 24 and 48 hours.

Parameters: wash with 1 gram each strand of the control solution with 1% component and 10% SLES, wherein control groups without complex 1 and sample group with complex 1, with 1 minute of massage and 2 minute of washing.

Results to be evaluated: olfactory perceptible differences between the control group versus samples, initially, after 24 and 48 hours.

Methods and Equipment

Olfactory comparative evaluation of fragrances applied to hair strands with washing made with a group of untrained volunteers.

Materials

Caucasian hair Strands (International Hair Importers & Products Inc.—IHIP).

Experiment Description 8 strands of IHIP were divided into four groups. The strands of hair were obtained from the same batch of hair.

Where:

a. Citrol test—two strands, washed with 1 g 10% SLES solution containing in the control 1% citrol and in the sample 1% citrol pre-dispersed in 1% complex 1, with 2 minutes of massage and 2 minutes of washing. Then the strands were evaluated by a panel of volunteers. After 24 hours of drying at room temperature, further assessment was made. And after 48 hours the last assessment was carried out.

b. Limonene test—two strands, washed with 1 g 10% SLES solution containing in the control 1% limonene and in the sample 1% limonene pre-dispersed in 1% complex 1, with 2 minutes of massage and 2 minutes of washing. Then the strands were evaluated by a panel of volunteers. After 24 hours of drying at room temperature, further assessment was made. And after 48 hours the last assessment was carried out.

c. Linalool test—two strands, washed with 1 g 10% SLES solution containing in the control 1% linalool and in the sample 1% linalool pre-dispersed in 1% complex 1, with 2 minutes of massage and 2 minutes of washing. Then the strands were evaluated by a panel of volunteers. After 24 hours of drying at room temperature, further assessment was made. And after 48 hours the last assessment was carried out.

d. Fragrance test—two strands, washed with 1 g 10% SLES solution containing in the control 1% fragrance and in the sample 1% fragrance pre-dispersed in 1% complex 1, with minutes of massage and 2 minutes of washing. Then the strands were evaluated by a panel of volunteers. After 24 hours of drying at room temperature, further assessment was made. And after 48 hours the last assessment was carried out.

Results and Discussion

The comparative assessments are tabulated in accordance with the number of volunteers by strand, which identified as higher intensity and better odor, and no odor.

TABLE 7

The Initial Result - Just After Washing (Wet Hair)

| | Control without complex 1 | Sample with complex 1 | Volunteers who have not experienced any odor |
|---|---|---|---|
| A - Citrol | 2 | 4 | 0 |
| B - Limonene | 1 | 3 | 2 |
| C - Linalool | 1 | 3 | 2 |
| D - Fragrance | 0 | 6 | 0 |

TABLE 8

Comparative Result after 24 Hours

| | Control without complex 1 | Sample with complex 1 | Volunteers who have not experienced any odor |
|---|---|---|---|
| A - Citrol | 1 | 4 | 1 |
| B - Limonene | 0 | 2 | 4 |
| C - Linalool | 0 | 3 | 3 |
| D - Fragrance | 0 | 6 | 0 |

TABLE 9

Comparative Result after 48 Hours

| | Control without complex 1 | Sample with complex 1 | Volunteers who have not experienced any odor |
|---|---|---|---|
| A - Citrol | 0 | 3 | 3 |
| B - Limonene | 0 | 1 | 5 |
| C - Linalol | 0 | 3 | 3 |
| D - Fragrance | 0 | 5 | 1 |

According to the results of comparative evaluations in the use of fragrance with and without a complex 1 according to the present invention, one can observe that the product positively interfere to the perception of the fragrance and long lasting in the capillary strand, especially when added along with components with different vapor pressure.

Example 4

Study of the Functional Properties of the Complex in Accordance with the Present Invention in a Shampoo Base Effect in the Intensity and Longevity of the Fragrance Substantivity in the Capillary Substrate A fragrance from citrus flower olfactory family in shampoo base, varying the combination (each one with a sample of a proposed formula for the complex of the present invention) was applied to bleached Caucasian hair strands.

The fragrance was previously diluted to 1.5% with each version of the complex to be tested according to the present invention to 1%, based on the shampoo, except for the control sample which was composed only by fragrance to 1.5% in a shampoo base. For four samples groups, three groups containing 1% of the complex 4, complex 3 and complex 2 used as a pre-dispersing ingredient for the fragrance and the fourth not (control group). Then each sample was applied on a strand and rinsed. Immediately after rinsing, as well as after 24 hours and 48 hours, the strands were evaluated by a panel of six volunteers. The procedure was applied to access interference of the complex according to the invention the substantivity properties of fragrances as well as the longevity (long lasting) in the strands.

Experiment

Colorless Caucasian hair strands (International Hair Imports) divided into 4 groups of 3 strands each, one control group and the other samples.

It was applied the shampoo with complex 4 in group A, shampoo with complex 3 in group B, shampoo with complex 2 in group C and group D was used shampoo control. In each group, two applications were made as described in the design of the experiment. Then the treated strands were evaluated for comparative olfactory by a group of six volunteers, just after washing, 24 hours and 48 hours after washing.

Design of experiment

Objective: to compare standard Caucasian strands—International Hair Importers & Products Inc. (IHIP). IHIP treated with reference shampoo formulation without complex according to the present invention with washing versus IHIP treated with formulations containing 1% complex according to the present invention with washing, initially, after 24 and 48 hours.

Parameters: wash with 1 gram each strand of the control solution with 1% component and 10% SLES, followed by two washings with shampoo, each group named with the same letter of the applied shampoo, A, B, C and D (as specified in the previous examples) for the control group without the complex according to the present invention, with 1 minute of massage and 2 minute of washing.

Results: olfactory perceptible differences between the control group versus samples, initially, after 24 and 48 hours.

Methods and Equipments

Olfactory comparative evaluation of fragrances applied to hair strands with washing made with a group of untrained volunteers.

Materials

Caucasian hair Strands (IHIP).

Experiment Description 12 strands of IHIP were divided into four groups. The strands of hair were obtained from the same batch of hair. Where:

a. Group D—Three strands, washed with 1 g 10% SLES solution with 2 minutes of massage and 2 minutes of washing. A second washing with shampoo D containing 1.5% fragrance with 2 minutes of massage and 2 minutes of washing. The washing was repeated. Then the strands were evaluated by a panel of volunteers. After 24 hours of drying at room temperature, further assessment was made. And after 48 hours the last assessment was carried out.

b. Group C—Three strands, washed with 1 g 10% SLES solution with 2 minutes of massage and 2 minutes of washing. A second washing with shampoo C containing 1.5% fragrance and 1% complex 2 with 2 minutes of massage and 2 minutes of washing. The washing was repeated. Then the strands were evaluated by a panel of volunteers. After 24 hours of drying at room temperature, further assessment was made. And after 48 hours the last assessment was carried out.

c. Group B—Three strands, washed with 1 g 10% SLES solution with 2 minutes of massage and 2 minutes of washing. A second washing with shampoo B containing 1.5% fragrance and 1% complex 3 with 2 minutes of massage and 2 minutes of washing. The washing was repeated. Then the strands were evaluated by a panel of volunteers. After 24 hours of drying at room temperature, further assessment was made. And after 48 hours the last assessment was carried out.

d. Group A—Three strands, washed with 1 g 10% SLES solution with 2 minutes of massage and 2 minutes of washing. A second washing with shampoo A containing 1.5% fragrance and 1% complex 4 with 2 minutes of massage and 2 minutes of washing. The washing was repeated. Then the strands were evaluated by a panel of volunteers. After 24 hours of drying at room temperature, further assessment was made. And after 48 hours the last assessment was carried out.

Results and discussion

The comparative assessments are tabulated in accordance with the number of volunteers by strand, which identified as higher intensity. It was multiplied by 4 in decreasing order, by 3, by 2 and by 1 and or better odor, and also with the one who not felt odor in any of the strands.

TABLE 10

Results of the evaluation
Just after washing

| | Number of volunteers | Score | Volunteers who have not experienced any odor |
|---|---|---|---|
| Group A: Complex 4 | 6 × 4 | 24 | 0 |
| Group B: Complex 3 | 5 × 3 + 1 × 2 | 17 | 0 |
| Group C: Complex 2 | 1 × 3 + 5 × 2 | 13 | 0 |
| Group D: Control | 6 × 1 | 6 | 0 |

TABLE 11

Result of comparative evaluation
After 24 hours

| | Number of volunteers | Score | Volunteers who have not experienced any odor |
|---|---|---|---|
| Group A: Complex 4 | 6 × 3 | 18 | 1 |
| Group B: Complex 3 | 4 × 3 + 1 × 2 | 14 | 1 |
| Group C: Complex 2 | 1 × 3 + 3 × 2 | 9 | 2 |
| Group D: Control | 4 × 1 | 4 | 2 |

TABLE 12

Result of comparative evaluation
After 48 hours

| | Number of volunteers | Score | Volunteers who have not experienced any odor |
|---|---|---|---|
| Group A: Complex 4 | 6 × 1 | 6 | 5 |
| Group B: Complex 3 | 0 | 0 | 6 |
| Group C: Complex 2 | 0 | 0 | 6 |
| Group D: Control | 0 | 0 | 6 |

According to the results of comparative evaluations with the application of the fragrance with or without complex variants according to the present invention, one conclude that the complex interfere in a positive manner in the perception and long lasting of keratinous substrate (capillary strand), especially in complex 4.

Example 5

Sensory Evaluation of Perfume in Hair

This evaluates the smell of cosmetic products after application to hair, using the method "sniff test".

Experimental Design 09 strands of bleached Caucasian hair were prepared, (DeMeoBrothers INC, NY, USA), weighing 5 grams and measuring 25 cm. All strands are subjected to a standard process for pre-cleaning using a 10% solution of sodium lauryl ether sulphate (SLES) for 1 minute followed by rinsing in water.

The strands were dried in a standard atmosphere at 55+/−% relative humidity and 22+/2° C. for 24 hours.

Strands were divided into three groups:
a. untreated—control (CTRL).
b. treated with complex 4, Code 25102010-1 (T01).
c. treated with complex 4, Code 25102010-B (T02).

Selection of Volunteers 16 trained volunteers were selected to evaluate the fragrance in the hair strands. Each volunteer evaluated the fragrance intensity of the nine strands 2, 4, 8, 24 and 48 hours after application of the products.

Classification of the Intensity of Perfume

Strands were classified according to the intensity of perfume in a 10-point scale in which 0 (zero) corresponds to the absence of perfume (no noticeable) and ten (10) a very strong fragrance. FIG. 1 represents the intensity scale of perfume used in the study.

The strands of the CTRL group were used only with reference to the volunteers as standard unscented hair.

The entire study was conducted in air-conditioned environment at 55+/−5% relative humidity and 22+/−2° C.

Preparation of Samples

Nine strands of bleached Caucasian hair were prepared (DeMeoBrothers INC, NY, USA), weighing 5 grams and measuring 25 cm. All strands are subjected to a standard process for pre-cleaning using a 10% solution of sodium lauryl ether sulphate (SLES) for 1 minute followed by rinsing in water. The strands were dried in a standard atmosphere at 55+/−% relative humidity and 22+/−2° C. for 24 hours prior to testing.

Treatment of Strands a) The water should be 35-40° C.;
b) Each strand was wet for 20 seconds and then the excess water was removed;
c) 1.0 ml of shampoo was applied and massaged for 60 seconds. Each strand was washed for 60 seconds and excess water removed.

Results and Discussion

From the results of the scores assigned by volunteers histograms were constructed to compare the effects of treatments.

Figure 2:
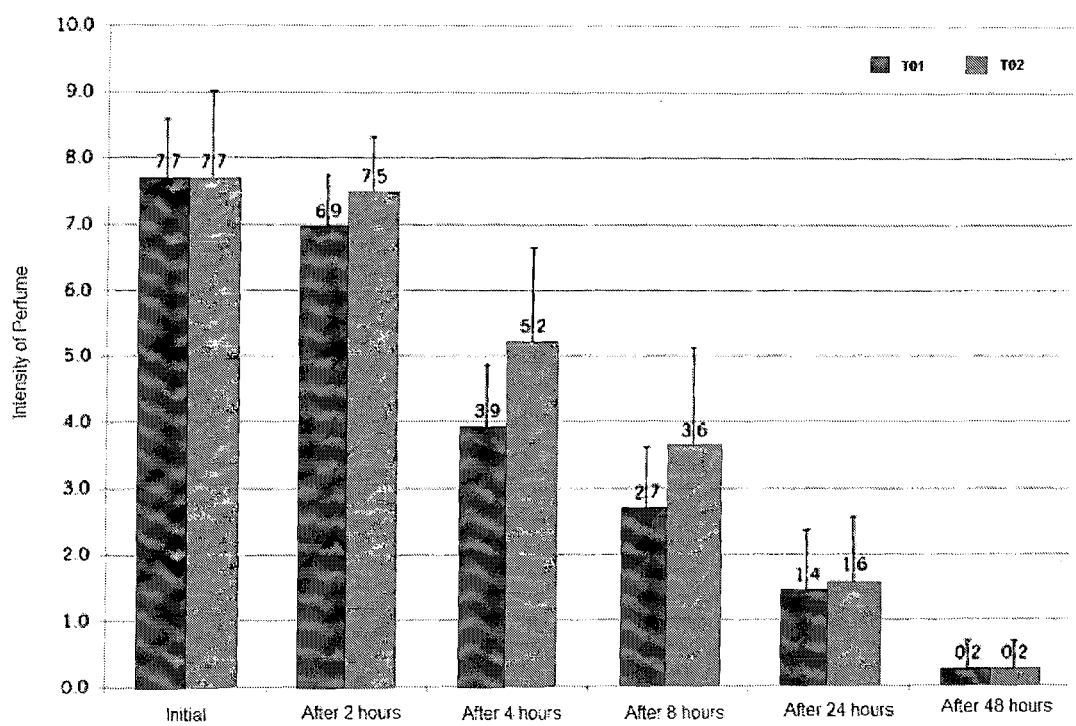
FIG. 2 presents data obtained for the notes assigned to each treatment, at each evaluation time.

FIG. 2 illustrates the data obtained for the score assigned to each treatment at each evaluation time.

The mean values of the intensity of perfume were statistically analyzed for each duration of the study, using the method of the Student t-test, bimodal, unpaired, whereas a range of 95%. Results of treatment group (TRAT) were compared to controls (CTRL).

Table 13 below summarizes the obtained results.

TABLE 13

Results of statistical analysis - T01 versus T02
P values for 95% I.C.

| Time of study | P Value | Did it show a significant difference? |
|---|---|---|
| Initial | P > 0.05 | NOT |
| After 2 hours | P > 0.05 | NOT |
| After 4 hours | P < 0.05 | YES |
| After 8 hours | P < 0.05 | YES |
| After 24 hours | P > 0.05 | NOT |
| After 48 hours | P > 0.05 | NOT |

According to statistical analysis, strands under treatments T01 and T02 showed no difference in intensity of perfume in the initial state (after application of the products) and 2 hours after product application.

Strands treated T01 and T02 did not differ in relation to perfume intensity after 24 and 48 hours after application of the products.

A rating scale of intensity was made from the score results (FIG. 1).

Table 14 below summarizes the obtained results.

TABLE 14

Summary of the classification of the intensity of perfume

| Time of study | T01 | T02 |
|---|---|---|
| Initial | Between Moderate and Strong | Between Moderate and Strong |
| After 2 hours | Between Moderate and Strong | Between Moderate and Strong |
| After 4 hours | between very weak and weak | between very weak and weak |
| After 8 hours | between very weak and weak | between very weak and weak |
| After 24 hours | between nothing perceptible and very weak | between nothing perceptible and very weak |
| After 48 hours | between nothing perceptible and very weak | between nothing perceptible and very weak |

Taking into account that the indication that the sample has no odor is when the intensity of perfume is equal to zero, a statistical analysis was carried out using the hypothesis test for a sample (one-sample t-test), with a 95% confidence interval.

The hypothetical value equal to zero was considered.

The statistical analysis results show that treatments T01 and T02 were statistically perfume intensity greater than zero after 2 and 4.8 times the 24 hours of the study.

After 48 hours the strands treated in T01 and T02 were statistically perfume intensity equal to zero. This indicates that after 48 hours of application of the products, the intensity of the strands of perfume has become imperceptible.

Thus, one can conclude that the strands under treatments T01 and T02 remain fragrant for up to 24 hours, and this intensity of perfume can be classified between "nothing perceptible" and "very weak".

Conclusion

In this study, strands of bleached Caucasian hair were treated with the products:
Complex 4, Code 25102010-1—Group T01
Complex 4, Code 25102010-B—Group T02

According to the obtained results, strands subjected to treatment T02 obtained perfume intensity significantly greater than strands subjected to treatment T01, 4 and 8 hours after application of the products.

There were no significant differences in intensity between the strands of perfume under treatments T01 and T02 after 2, 24 and 48 hours of application of the products in hair.

Strands under treatments T01 and T02 remained fragrant for up to 24 hours and this intensity of perfume can be classified between "anything perceptible" and "very weak".

The results of these tests demonstrate the effectiveness of the composition of the invention for use as cosmetic active ingredient.

It should be understood that the embodiments described above are merely illustrative and that other embodiments may occur to one skilled in the art, for functions and substantially equivalent results. Therefore, the present invention should not be considered limited to the embodiments described in this.

The one skilled in the art can readily assess, through the teachings contained in the text and examples presented, and advantages of the invention to propose variations and equivalent alternative embodiment, without departing from the scope of the invention as defined in the appended claims.

The invention claimed is:

1. Complex for improvement of distribution and retention of fragrances into keratinous matter consisting essentially of:
   (A) a $C_{10}$-$C_{18}$ alkyl pyrrolidone present in an amount of 40 to 60% by weight,
   (B) at least one polyol compound having two hydroxyl groups, and/or three hydroxyl groups present in the amount of 40 to 60% by weight; and
   (C) optionally at least one fatty alcohol.

2. Complex according to claim 1, wherein the $C_{10}$-$C_{18}$ alkyl pyrrolidone is lauryl pyrrolidone.

3. Complex according to claim 1, wherein the fatty alcohol is selected from those having carbon chain from $C_{10}$ to $C_{22}$.

4. Complex according to claim 1, wherein said polyol compound comprises a mixture of propylene glycol (two hydroxyl), 1,2,3-propanetriol (three hydroxyl groups) in a 1:1 ratio.

5. A method of treating keratinous matter comprising administration to said keratinous matter said complex according to claim 1 as an additive that provides improved distribution and retention of fragrances into keratinous matter. 0.01% to 99.99%.

6. The method according to claim 5, wherein the amount of complex in relation to the amount of fragrance ranges from 0.01% to 99.99%.

7. The method according to claim 6, wherein the ratio between the amount of complex and the amount of fragrance ranges from about 0.5:1 to about 1:0.5.

8. The method according to claim 7, wherein the ratio between the amount of complex and the amount of fragrance ranges from about 1:1 to 0.75:1.

9. Cosmetic Product comprising the complex according to claim 1.

10. Cosmetic Product according to claim 9, comprising an amount of complex in relation to an amount of fragrance ranging from about 0.01% to 99.99%.

11. Cosmetic Product according to claim 10, comprising a ratio of complex in relation to fragrance ranging from about 0.5:1 to about 1:0.5.

12. Cosmetic Product according to claim 11, comprising a ratio of complex in relation to fragrance is 1:1 or 0.75:1.

13. Method for improvement of the distribution and retention of fragrances into keratinous matter consisting in diluting at least one fragrance in a complex according to claims 1 prior to application on the keratinous matter or cosmetic product.

14. Method according to claim 13, wherein the amount of complex in relation to the amount of fragrance used in the dilution ranges from 0.01% to 99.99%.

15. Method according to claim 14, wherein the ratio of complex in relation to the fragrance used in the dilution ranges from about 0.5:1 to 1:0.5.

16. Method according to claim 15, wherein the ratio of complex in relation to fragrance used in the dilution ranges from preferably 1:1 or 0.75:1.

* * * * *